US006537294B1

(12) United States Patent
Boyle et al.

(10) Patent No.: US 6,537,294 B1
(45) Date of Patent: Mar. 25, 2003

(54) DELIVERY SYSTEMS FOR EMBOLIC FILTER DEVICES

(75) Inventors: William J. Boyle, Fallbrook, CA (US); Benjamin C. Huter, Murrieta, CA (US); Scott J. Huter, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 165 days.

(21) Appl. No.: 09/691,463

(22) Filed: Oct. 17, 2000

(51) Int. Cl.$^7$ .............................................. A61M 29/00
(52) U.S. Cl. ...................................................... 606/200
(58) Field of Search ................................ 606/191, 192, 606/194, 195, 198, 200

(56) References Cited

U.S. PATENT DOCUMENTS

| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |

(List continued on next page.)

FOREIGN PATENT DOCUMENTS

| EP | 0 472 334 A1 | 2/1992 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |

Primary Examiner—John J. Calvert
Assistant Examiner—Shaun R Hurley
(74) Attorney, Agent, or Firm—Fulwider Patton Lee & Utecht, LLP (57) ABSTRACT

A delivery system for an expandable filter device includes a dual lumen delivery sheath which has a lumen for receiving the expandable filter device and a lumen for receiving a primary guide wire. The primary guide wire is utilized to place the delivery sheath and expandable filter into the desired region of the patient's vasculature via an over-the-wire or rapid-exchange arrangement. The delivery sheath can be protracted over the expandable filter device to allow the filter to be deployed within the patient's vasculature at the desired location. The delivery system can be embodied in an alternative design in which the primary guide wire extends through a guide wire lumen located in an obturator which forms part of the expandable filter device. Again, the primary guide wire is utilized to maneuver the filter device into the desired area via an over-the-wire arrangement. A slit extending longitudinally along the length of the sheath facilitates the removal of the guide wire and delivery sheath from the patient's vasculature.

32 Claims, 7 Drawing Sheets

U.S. PATENT DOCUMENTS

| | | |
|---|---|---|
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A * | 6/1998 | Nakhjavan .................. 606/159 |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,867 A * | 9/1998 | Zarbatany et al. .......... 606/191 |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,013,093 A | 1/2000 | Nott et al. |
| 6,142,987 A | 11/2000 | Tsugita |
| 6,146,383 A * | 11/2000 | Cragg et al. ................ 604/523 |
| 6,152,946 A | 11/2000 | Broome et al. |
| 6,171,327 B1 | 1/2001 | Daniel et al. |
| 6,179,859 B1 | 1/2001 | Bates et al. |

\* cited by examiner

DELIVERY SYSTEMS FOR EMBOLIC FILTER DEVICES

BACKGROUND OF THE INVENTION

The present invention relates generally to filtering devices and systems which can be used when an interventional procedure is being performed in a stenosed or occluded region of a blood vessel to capture embolic material that may be created and released into the bloodstream during the procedure. The system of the present invention is particularly useful when performing balloon angioplasty, stenting procedures, laser angioplasty, atherectomy, or other interventional procedures in critical vessels, particularly in vessels such as the carotid arteries, where the release of embolic debris into the bloodstream can occlude the flow of oxygenated blood to the brain or other vital organs, which can cause devastating consequences to the patient. While the embolic protection system of the present invention is particularly useful in carotid procedures, the invention can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the percutaneous introduction of the interventional device into the lumen of the artery, usually through a catheter. In typical carotid PTA procedures, a guiding catheter or sheath is percutaneously introduced into the cardiovascular system of a patient through the femoral artery and advanced through the vasculature until the distal end of the guiding catheter is in the common carotid artery. A guide wire and a dilatation catheter having a balloon on the distal end are introduced through the guiding catheter with the guide wire sliding within the dilatation catheter. The guide wire is first advanced out of the guiding catheter into the patient's carotid vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. The first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a collapsed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid or arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature. Other techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the inlet opening of the filter and enter the blood-stream as the filtering system is being collapsed and removed from the patient. In such a case, the act of collapsing the filter device may actually squeeze trapped embolic material through the opening of the filter and into the bloodstream.

Some of the prior art filters which can be expanded within a blood vessel are attached to the distal end of a guide wire or guide wire-like tubing which allows the filtering device to be placed in the patient's vasculature when the guide wire is manipulated in place. Once the guide wire is in proper position in the vasculature, the embolic filter can be deployed within the vessel to capture embolic debris. The guide wire can then be used by the physician to deliver interventional devices, such as a balloon angioplasty dilatation catheter or a stent, into the area of treatment.

While expandable filters placed on the distal end of a guide wire or guide wire like catheter are generally capable of reaching many stenosis in a patient's vasculature, there still can be some instances encountered by a physician in which the guide wire cannot reach or cross a particularly tight distal lesion. This can sometimes occur when the expandable filter device is to be placed across a tight lesion in the distal carotid arteries when a femoral approach is taken by the physician. In those cases, the physician often can steer the filter device to a location close to the area of treatment, but cannot cross the lesion for one reason or another. Some physicians deal with this situation by removing the filter device from the patient's vasculature and attempting to cross the lesion using a separate guide wire which can be used to somewhat straighten the body vessel, making it easier for the physician to re-attempt the placement of the filter device across the lesion. In such cases, the physician is required to maneuver the steerable filter device back to the area of treatment to re-attempt the crossing of the lesion. The filter device may be then able to cross the lesion and be placed downstream of the area of treatment to capture any embolic debris which can may be created during the subsequent interventional procedure. However, this procedure causes the physician to perform additional steps which are time-consuming due to the increased number of times that the physician has to maneuver the filtering device and additional guide wire into the patient's vasculature.

What has been needed is a reliable system for use with an expandable filter device which allows the physician to steer through tortuous anatomy to distal lumens where the filtering device can be deployed to capture or remove embolic debris from the bloodstream. The system should be relatively easy for a physician to use and should provide a suitable delivery system for placing a filtering device into distal and tight lesions of a patient's anatomy. Moreover, the system should be relatively easy to deploy and remove from the patient's vasculature. The invention disclosed herein satisfies these and other needs.

SUMMARY OF THE INVENTION

The present invention provides a delivery system which can be utilized to place an expandable filter device past a distal lesion in a patient's vasculature in order to capture embolic debris which may be created during the performance of a therapeutic interventional procedure, such as a balloon angioplasty or stenting procedure, in order to prevent embolic debris from entering the bloodstream and blocking vessels downstream from the area of treatment. The present invention can be used in conjunction with either a steerable or non-steerable expandable filtering device. The present invention eliminates the need for a physician to remove and re-insert the expandable filtering device in the patient since a separate guide wire is utilized to reach the desired area of treatment. The system creates an over-the-wire delivery system for placing the expandable filter device in the area of treatment. As a result, the present invention should eliminate additional steps when placing an expandable filtering device into certain distal locations in a patient's vasculature.

In one aspect of the present invention, a dual lumen delivery sheath is used with an expandable filter device and a separate guide wire as the delivery system. The dual lumen delivery sheath can be made from an elongate tubular member which is adapted to receive both the expandable filter device and the guide wire which can be used as a primary component for placing the filtering device into the area of treatment. In one aspect of the present invention, two separate lumens are formed in the delivery sheath, one for receiving the expandable filtering device and the other for the primary guide wire. In this arrangement, the primary guide wire is extendable within its own separate lumen so that it can be maneuvered by the physician through the tortuous anatomy of the patient into the area of treatment. The delivery sheath can be placed into the area of treatment using over-the-wire techniques which places both the delivery sheath and the expandable filter device past the lesion to be treated. Thereafter, the primary guide wire can be removed from the patient's vasculature with the delivery sheath and expandable filter device remaining in place downstream from the area of treatment. The delivery sheath can then be retracted to allow the expandable filter device to move into its expanded condition within the body lumen where it will be deployed for capturing any embolic debris which may be collected during the subsequent interventional procedure. If the filter device is mounted on its own guide wire, an interventional device can be delivered into the area of treatment using over-the-wire techniques.

In another aspect of the invention, the guide wire lumen extends along the entire length of the delivery sheath. Alternatively, a rapid exchange type delivery sheath can be created which utilizes only a short segment which receives the primary guide wire. Usually, the guide wire segment is located at the distal end of the delivery sheath to ensure that both the distal ends of the sheath and filter device will properly track along the primary guide wire. In another aspect of the present invention, the distal end of the filter lumen has a smaller diameter than the collapsed filter device to prevent the filter device from entering into the guide wire lumen until the expandable filter device is ready to be deployed within the patient's vasculature. This narrow lumen helps prevent the primary guide wire and filter device from possibly becoming "tangled" during delivery with the patient's vasculature. The narrow portion of the lumen should not affect the ability of the sheath to be retracted over the collapsed filter device since the narrower lumen should stretch somewhat over the filter device. Alternatively, the narrow portion of the sheath may be scored or provided with one or more lines of perforations which will cause the sheath to split a controlled amount making it easier to retract the sheath over the filter device.

The filter lumen of the present invention also can be made from a short segment to create a rapid exchange type delivery sheath. In one aspect, the filter lumen would be created from a short segment formed adjacent to the guide wire lumen. In an alternative design, both the guide wire lumen and filter lumen could be short segments forming a rapid exchange type sheath. The sheath could be mounted to a mandrel or third wire which would be used to retract the sheath from the expandable filter.

The delivery sheath made in accordance with the present invention also can be provided with a slit extending substantially along the length of the sheath to provide a slotted exchange sleeve which facilitates exchanges of the delivery sheath during use. As a result, the time needed to remove the delivery sheath from the patient's vasculature can be reduced.

In an alternative delivery design, the primary guide wire can be utilized in accordance with an expandable filter device which utilizes an obturator for delivering the filter device within the patient's vasculature. An obturator is generally a tapered tip made from a soft pliable material which creates an atraumatic tip which helps prevent trauma from being inflicted on the walls of the patient's vasculature as the filter device is being steered therethrough. In this aspect of the present invention, the obturator is equipped with a lumen through which the primary guide wire can extend to provide an over-the-wire delivery system that is easy to operate. The guide wire lumen on the obturator could be either set off center from the distal tip of the obturator or could extend substantially through the center portion of the tip of the obturator. In use, the entire filter device, including its own delivery sheath, rides over the primary guide wire (via the guide wire lumen of the obturator) and into the desired area of deployment within the patient's vasculature.

These and other inventions of the present invention will become more apparent from the following detailed description, when taken in conjunction with the accompanying exemplary drawings.

DETAILED DESCRIPTION OF THE PREFERRED EMBODIMENTS

Figure 1:
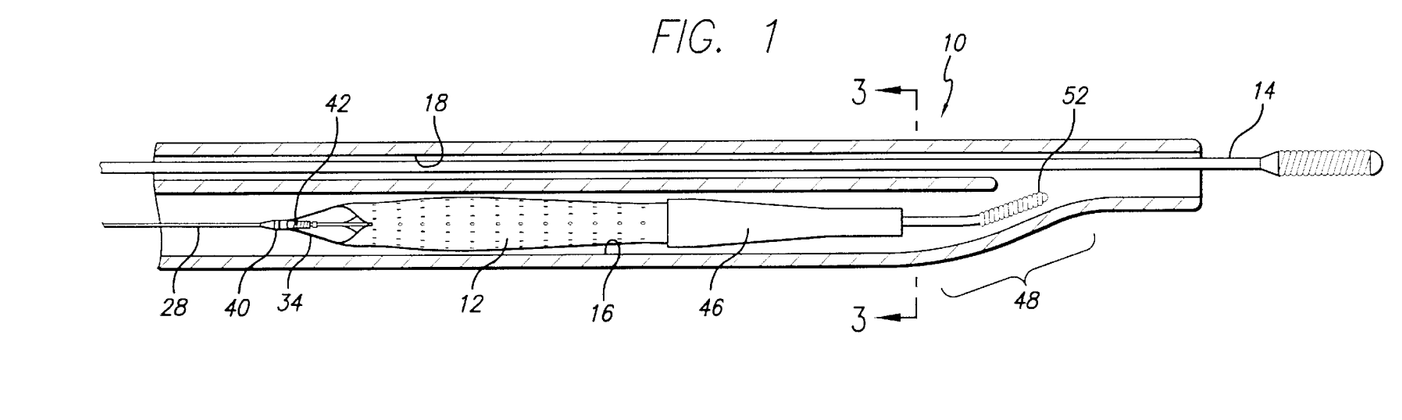
FIG. 1 is an elevational view, partially in cross-section, of one embodiment of a dual lumen delivery sheath embodying features of the present invention showing an expandable filtering device held in its collapsed position within the delivery sheath along with a primary guide wire extended within the guide wire lumen.
Figure 4:
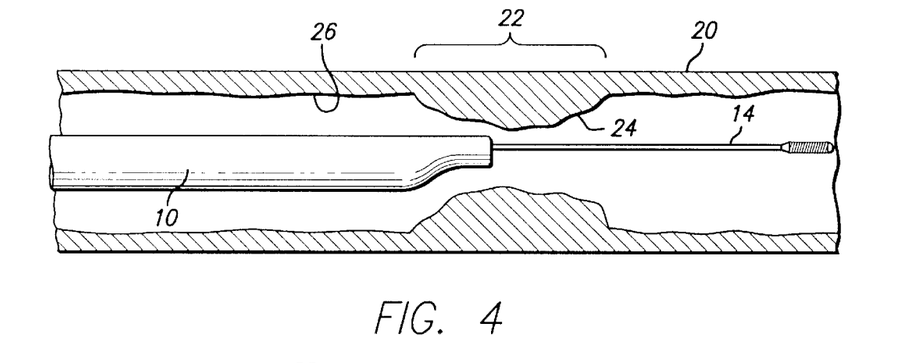
FIG. 4 is an elevational view, partially in cross-section showing the delivery sheath and expandable filter device of FIG. 1, along with the primary guide wire placed past a stenosis located in a body vessel.
Figure 5:
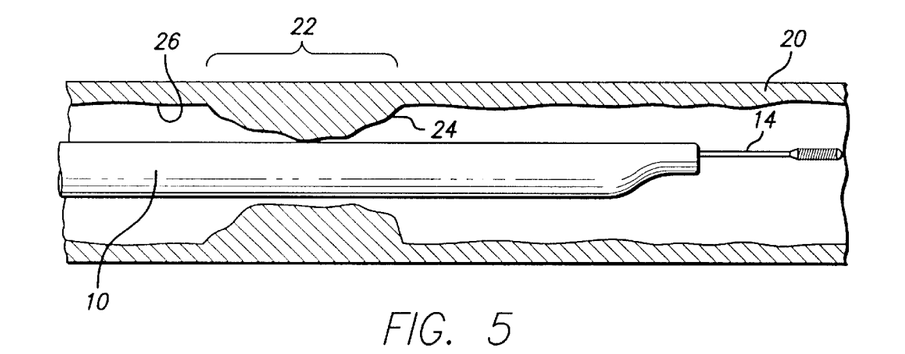
FIG. 5 is an elevational view, partially in cross-section, showing the dual lumen delivery sheath of the present invention placed across the stenosis in the body vessel.
Figure 6:
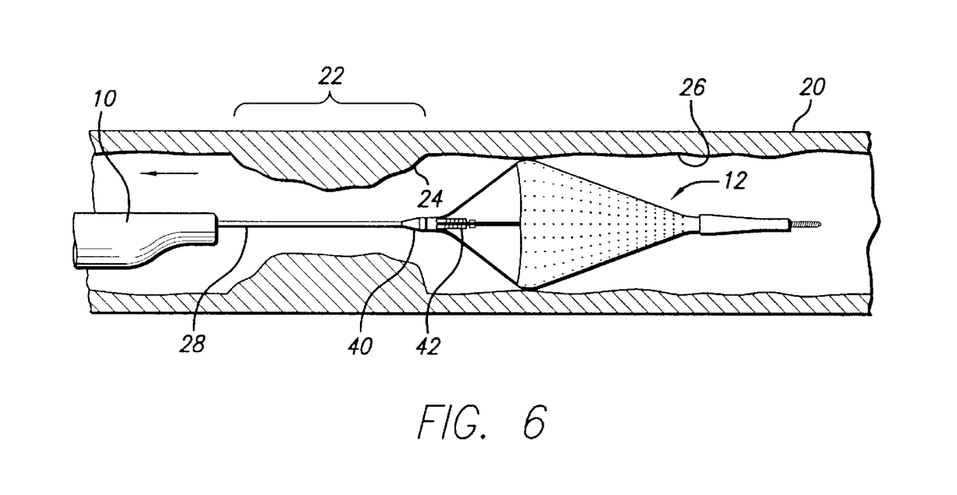
FIG. 6 is an elevational view, partially in cross-section, showing the dual lumen delivery sheath of the present invention retracted past the expandable filter device allowing the filter device to move into its expanded position within the body vessel.

Turning now to the drawings, in which like reference numerals represent like and corresponding elements in the drawings, FIG. 1 represents a dual lumen delivery sheath 10 incorporating features of the present invention. In the particular embodiment shown in FIG. 1, the dual lumen delivery sheath 10 is adapted to receive both an expandable filter device 12 and a primary guide wire 14. The delivery sheath 10 includes a pair of lumens, namely, a filter lumen 16 which is adapted to receive the expandable filter device 12 and a guide wire lumen 18 which receives the primary guide wire 14. As is shown in FIGS. 4–6, the delivery sheath 10 can be placed within an artery 20 or other blood vessel of a patient. This portion of the artery 20 has an area of treatment 22 in which arthroscopic plaque 24 has built up against the inside wall 26 of the artery 20. In use, the filter device 12 is to be placed distal to, and downstream from, the area of treatment 22, as shown in FIG. 6. Methods for deploying the system of FIG. 1 will be described in greater detail below.

The present invention is described herein in conjunction with a self-expanding filter device 12 which is capable of self-expanding from a contracted or collapsed position to an expanded or deployed position within the patient's vasculature. The filter lumen 16 of the delivery sheath 10 is thus utilized to maintain the expandable filter device 12 in its collapsed state for delivery into the patient's vasculature. Later, when the device is to be deployed at the particular location downstream from the area of treatment, the sheath 10 is retracted to allow the filter device to expand to its open or expanded position within the body vessel. It should also be appreciated that other types of expandable filter devices could be used in conjunction with the present invention in order to deliver the filter device to the desired location in a patient's vasculature. Additionally, the filter device need not be self-expanding, but could utilized mechanical components to open and close the filter as desired. For that reason, the type of filter device utilized in accordance with the present invention can include a number of different embodiments and is not limited to the particular filter device disclosed herein.

Figure 2:
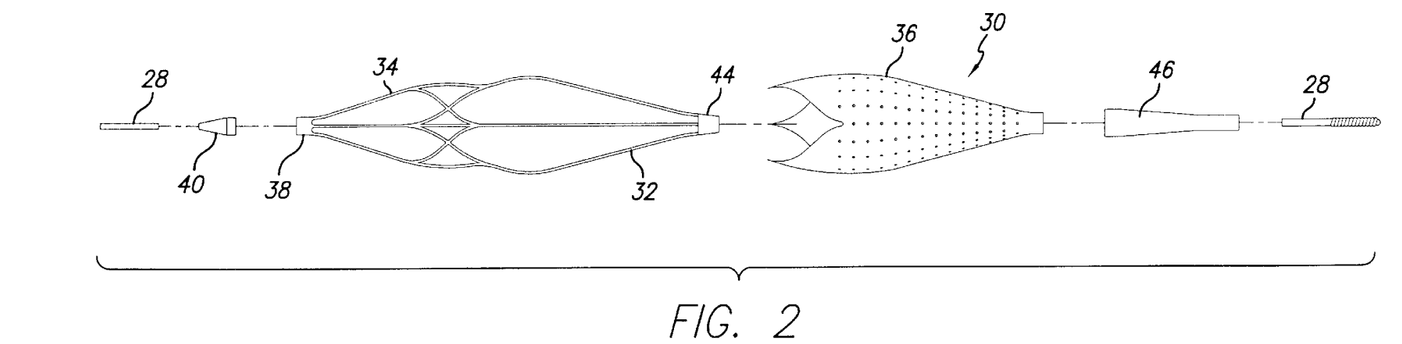
FIG. 2 is an exploded elevation view of the expandable filter device of FIG. 1 which depicts just one type of filter device that can be used with the present invention.

As can be seen best in FIG. 2, one particular type of filter device 12 which can be used with the present invention is shown mounted on a separate guide wire 28 that can be utilized by the physician to introduce interventional devices into the area of treatment. This expandable filter device 12 includes an expandable filtering assembly 30 having an expandable strut assembly 32 consisting of a number of struts 34 which expand radially outward to open a filter 36 that is attached to the strut assembly 32.

As can be seen in FIGS. 1 and 2, the expandable strut assembly 32 is attached to the guide wire 28 at its proximal collar 38 which is fixed between two stop fittings 40 and 42. This allows the distal collar 44 of the strut assembly to move axially along the guide wire 28 and allows the struts 34 to expand and collapse as needed. This arrangement also allows the filter assembly to spin on the guide wire 28. Attached to the distal end of the strut assembly 30 is an obturator 46 which provides an atraumatic tip which prevents trauma from being inflicted on the walls of the patient's vasculature. The obturator 46 is bonded or otherwise attached to the filtering assembly 30.

In one particular procedure in using the present invention, a balloon angioplasty catheter (not shown), for example, can be introduced within the patient's vasculature in a conventional SELDINGER technique through a guide wire catheter not shown). The guide wire 28 of the deployed filter device 12 would be disposed through the area of treatment and the dilitating catheter can be advanced over the guide wire 28 within the artery until the balloon portion is directly in the area of treatment. The balloon of the dilitation catheter can be expanded, expanding the plaque and artery to create a larger opening in the area of treatment to reduce the blockage in the vessel at the position of the plaque and increase blood flow. After the dilitating catheter is removed from the patient's vasculature, a stent could also be delivered into the area of treatment using over-the-wire techniques to help hold and maintain this portion of the artery and help prevent re-stenosis from occurring in the area of treatment. Any embolic debris which is created during the intereventional procedure will be released into the blood stream and will enter the filtering assembly located downstream from the area of treatment. Once the procedure is completed, the filter device 12 can be collapsed and removed from the patient's vasculature, taking with it all embolic debris trapped within the filter 36.

Although the procedure described herein is directed to an angioplasty and stenting procedure which can be performed in the patient's vasculature utilizing the present invention, it should be appreciated to those skilled in the art that any one of a number of interventional procedures could be utilized in the area of treatment as well. For example, laser angioplasty, atherectomy and still other interventional procedures could be performed in the area of treatment utilizing the present invention. Moreover, the present invention can be utilized in a number of other body vessels including, but not limited to, the coronary arteries, renal arteries, saphenous vein grafts and other peripheral arteries.

Referring now to FIGS. 4–6, one method of utilizing the present invention is herein disclosed. The dual lumen delivery sheath 10 of the present invention can be introduced with the filter device placed in its collapsed position within the artery 20 in which the interventional procedure is to be performed. Initially, the primary guide wire 14 is placed within the patient's vasculature and is maneuvered by the physician into the area of treatment 20. As is shown in FIG. 4, the primary guide wire 14 is maneuvered past the area of treatment 22 to a downstream location where the filter device will be deployed. After the primary guide wire is in place, the delivery sheath and filter device can be backloaded onto the proximal end of the guide wire. The physician can then move the delivery sheath 10 and the filter device 12 over the primary guide wire 14 using over-the-wire techniques known in the art. As can be seen in FIG. 5, the entire delivery sheath 10 and filter device 12 have been placed downstream from the area of treatment 22 to the location where the filter device 12 is to be deployed. Once the delivery sheath and filter device are in the desired location, the physician can remove the primary guide wire 14 from the patient to allow the filter device 12 to expand within the artery without any obstructions. As is shown in FIG. 6, the primary guide wire 14 has been removed and the delivery sheath 10 has been retracted proximally to allow the expandable filter device 12 to move into its open or expanded position within the artery 20. Thereafter, the entire delivery sheath 10 can be removed from the guide wire 28 of the filter device 12 allowing interventional devices to be positioned into the area of treatment 22 utilizing over-the-wire techniques. In the event that any embolic debris is created during the interventional procedure, the embolic debris will be released into the blood stream where it should collect within the filter element 36 of the filter device 12.

After the interventional procedure is completed, the physician can remove the interventional device from the guide wire 28. Thereafter, the physician may wish to leave the filter device 12 in place in the artery to insure that all embolic debris generated during the procedure is driven into the filter portion 36 of the filter device 12. Thereafter, once the physician is assured that all embolic debris has been collected, he/she can then place another sheath (not shown) over the guide wire 28 which would contact the strut assembly 32 causing the struts and the filter to move back to its collapsed position. Thereafter, the entire filter device 12 could be collapsed within the sheath and removed from the patient's vasculature.

Figure 8:
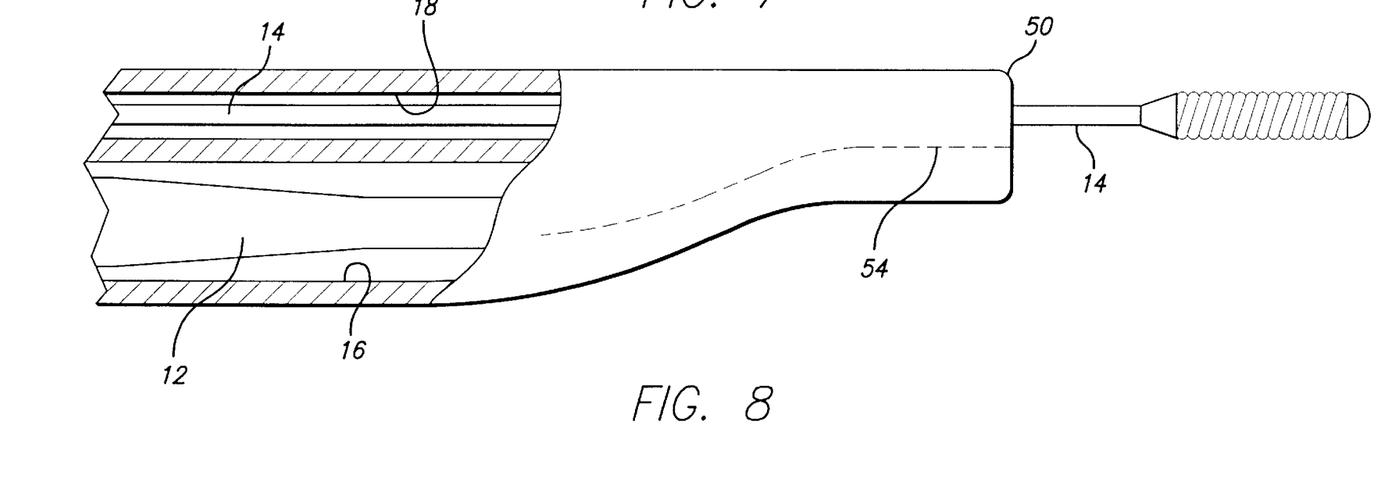
FIG. 8 is an elevational view showing a perforation or score line located on the dual lumen delivery sheath which aids in retracting the sheath over the collapsed filter device.

Referring specifically now to FIGS. 1 and 8, the distal most end of the delivery sheath 10 is shown. As can be seen in FIG. 1, the filter lumen 16 extends into the guide wire lumen 18 near the distal end to create a low profile component capable of reaching distal and tight lesions. The distal end of the filter lumen 16 has a region 48 with a diameter less than the diameter of the main portion of the filter lumen 16. This particular configuration can be utilized to create a small profile diameter at the distal most end 50 of the delivery sheath 10 and to prevent the sheath from "digging" or "snow plowing" into the artery walls as the delivery sheath 10 is being delivered over the primary guide wire 14. Otherwise, if the distal opening of the delivery sheath 10 is too large, it is possible for the distal end to inflict trauma to the artery walls as it is being pushed up through the anatomy. Moreover, this reduced region 48 on the filter lumen 16 also helps to prevent the filter device 12 from extending into the guide wire lumen and prevent the coil tip 52 of the guide wire 28 from becoming tangled with the primary guide wire 14 as the components are being manipulated into the patient's vasculature.

This reduced diameter region 48 of the filter lumen 16 should not prevent the sheath from retracting over the filter device 12 since the delivery sheath 10 can be made from a material which will stretch somewhat as the sheath 10 is being retracted over the filter device. However, this region 48 of the sheath 10 can be formed or scored with perforations 54 which extend longitudinally along the sheath at this area and will cause the sheath to split a controlled amount as the sheath 10 is being retracted over the filter device 12. FIG. 8 shows one particular way of scoring the lumen with perforations 54 which will open as the reduced region 48 is being retracted over the filter device. These perforations should assure that the sheath will be properly retracted over the filter device.

Figure 3A:
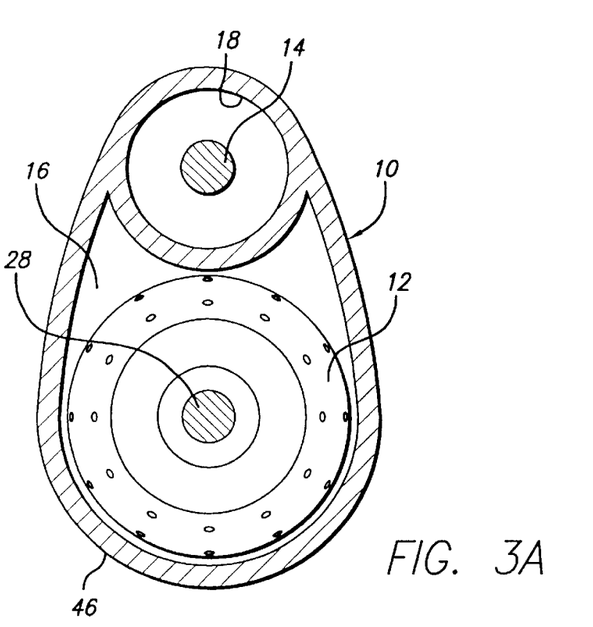
FIG. 3A is a cross-sectional view of the dual lumen delivery sheath of FIG. 1 taken along lines 3—3.
Figure 3B:
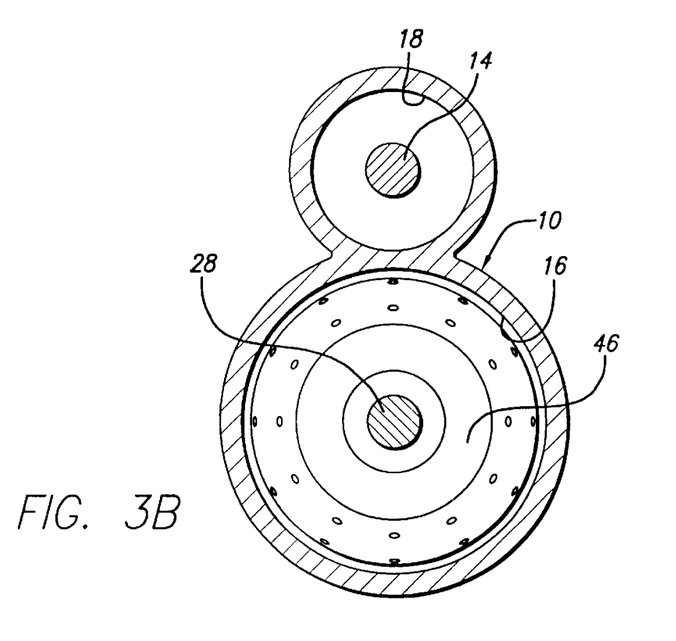
FIG. 3B is a cross-sectional view of another configuration of a dual lumen delivery sheath made in accordance with the present invention.

Referring now to FIGS. 3A and 3B, it can be seen that the guide wire lumen 18 can be formed within the interior of the delivery sheath 10 as is shown in FIG. 3A or it could alternatively be formed as a separate lumen which extends outside the filter lumen 16 as is shown in FIG. 3B. It should be appreciated that other configurations having lumens of different shapes and sizes can be utilized in accordance with the present invention which would not depart from the spirit and scope of the present invention.

Figure 7:
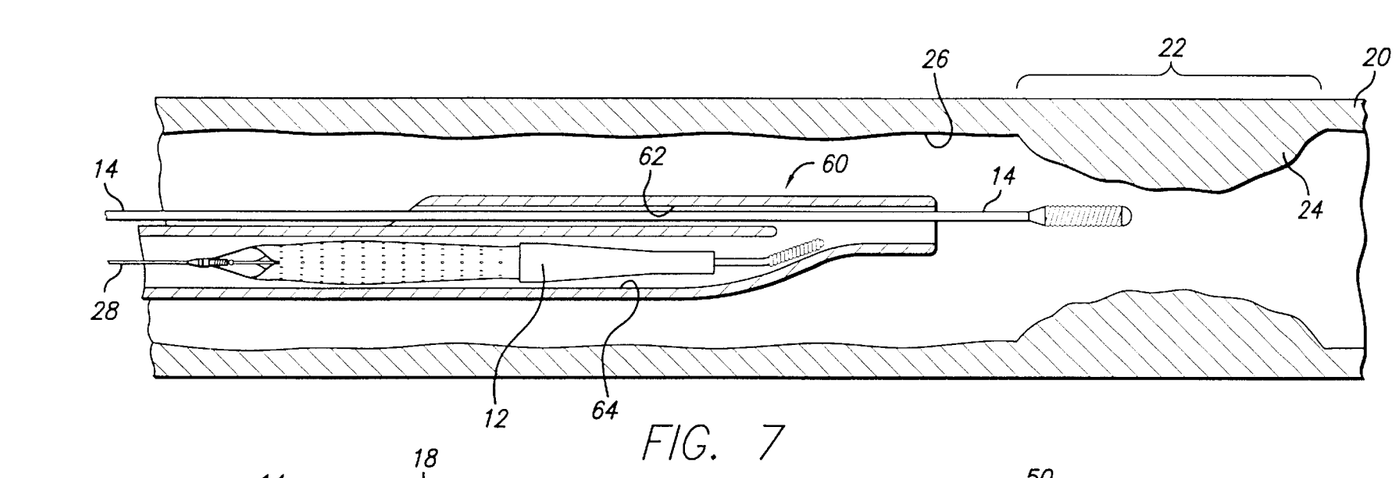
FIG. 7 is an elevational view, partially in cross-section, showing the distal end of a rapid-exchange embodiment of a dual lumen delivery sheath made in accordance with the present invention.

Referring now to FIG. 7, an alternative embodiment of a delivery sheath 60 made in accordance with the present invention is shown. In this particular embodiment, the delivery sheath includes both a guide wire lumen 62 and a filter lumen 64, however, the guide wire lumen 66 does not extend along the entire length of the sheath 60 as does the previous embodiment described herein. Rather, the guide wire lumen 62 is a short lumen incorporated into the sheath 60 to create a rapid exchange type delivery sheath. This particular sheath 60 has the same features of the embodiment previously described and would be capable of delivering the filter device 12 into the area of treatment in the same manner described herein.

Figure 9:
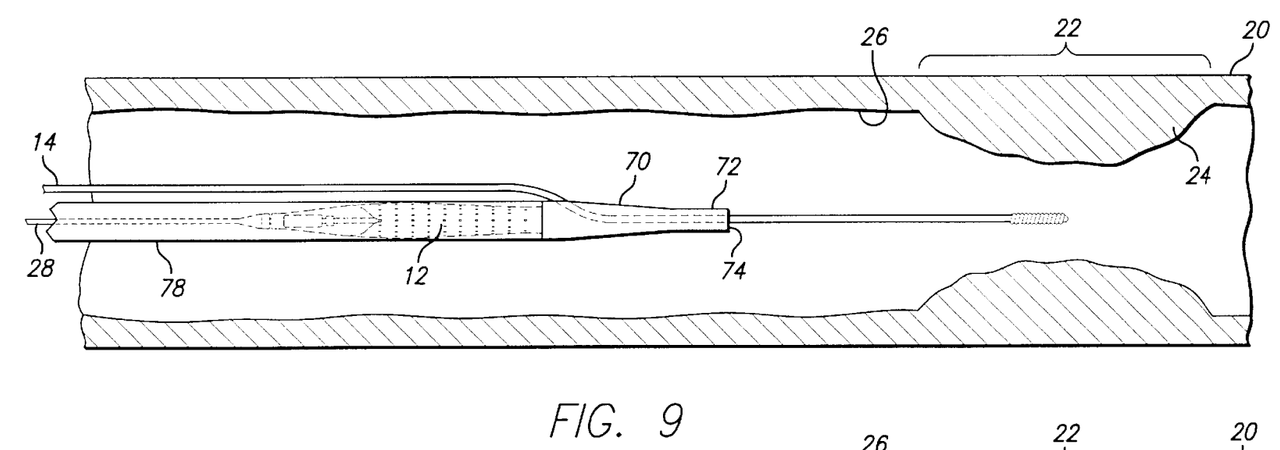
FIG. 9 is an elevational view, partially in cross-section, showing another embodiment of a delivery system made in accordance with the present invention.
Figure 10:
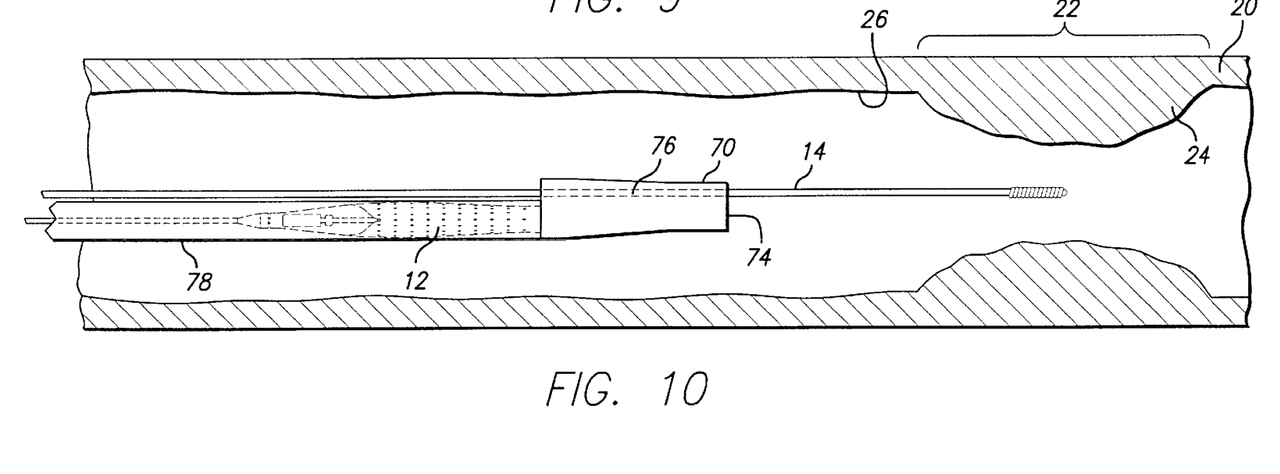
FIG. 10 is an elevational view, partially in cross-section, showing another embodiment of a delivery system made in accordance with the present invention.

Referring now to FIGS. 9 and 10, an alternative delivery system made in accordance with the present invention is shown. In these particular figures, the primary guide wire 14 is not disposed within the delivery sheath itself, but rather, is placed within a lumen created within an obturator 70 located on the distal end of the filter device 12. Referring initially first to FIG. 9, the obturator 70 is shown having a guide wire lumen 72 which extends within the obturator and receives the primary guide wire 14 during use. This obturator 70 creates an atraumatic tip as it is made from a soft material such as PEBAX or other soft polymeric material. Again this obturator helps prevent trauma to the inner walls of the patient's vasculature as the device is being delivered to the target area. The obturator 70 is attached to the filter device 12 via the strut assembly 32 and the distal end of the guide wire 28. This particular embodiment of the filter device 12 is substantially similar to the filter device shown in FIG. 2. The major difference is that the distal end of the guide wire 28 does not extend through the obturator 70 as does in the filter device shown in FIG. 2. Rather, the obturator 70 is attached to the strut assembly 32 and the distal end of the guide wire 28. This allows the guide wire lumen 72 to extend through the main portion of the obturator 70 and out the center of the distal tip 74 of the obturator.

As can be seen in FIG. 10, the guide wire lumen 76 can alternatively be laced off center from the obturator to create a lumen which extends substantially parallel with the longitudinal axis of the delivery sheath 78. However, both of these guide wire lumens 72 and 76 perform the same function of providing a means for delivering the filter device 12 into the desired area utilizing an over-the-wire technique.

The delivery system shown in FIGS. 9 and 10 can be used in a similar manner as described herein in that the primary wire would be first positioned across the lesion. The filter device 12 can then be backloaded onto the proximal end of the guide wire (via the obturator) and advanced over the wire to cross the lesion. The primary guide wire would then be removed and the sheath 78 would be retracted to deploy the filter device 12 within the artery. Again, interventional devices could be advanced over the guide wire 28 to perform the interventional procedure. Thereafter, the filter device could be collapsed by the restraining sheath and removed from the patient's vasculature.

Figure 11:
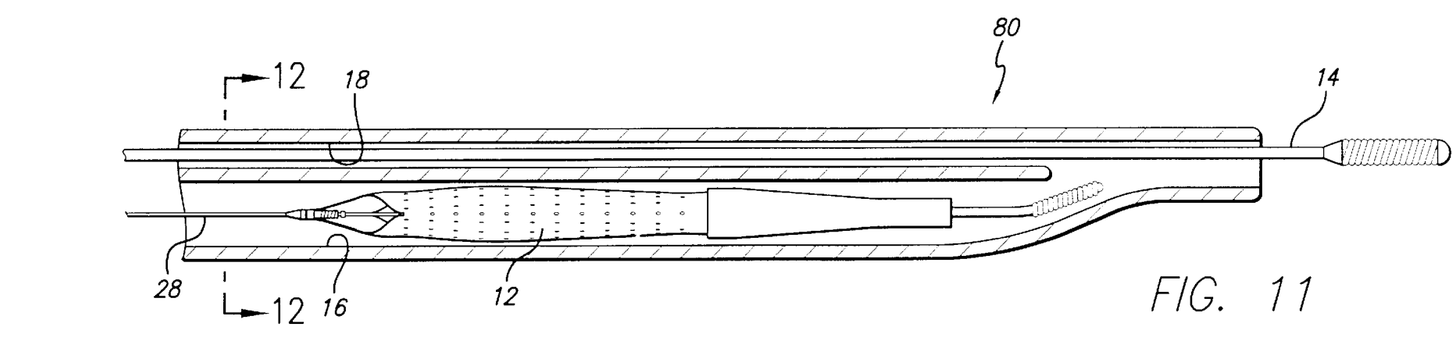
FIG. 11 is an elevational view, partially in cross-section, showing another embodiment of a dual lumen delivery sheath made in accordance with the present invention.
Figure 12:
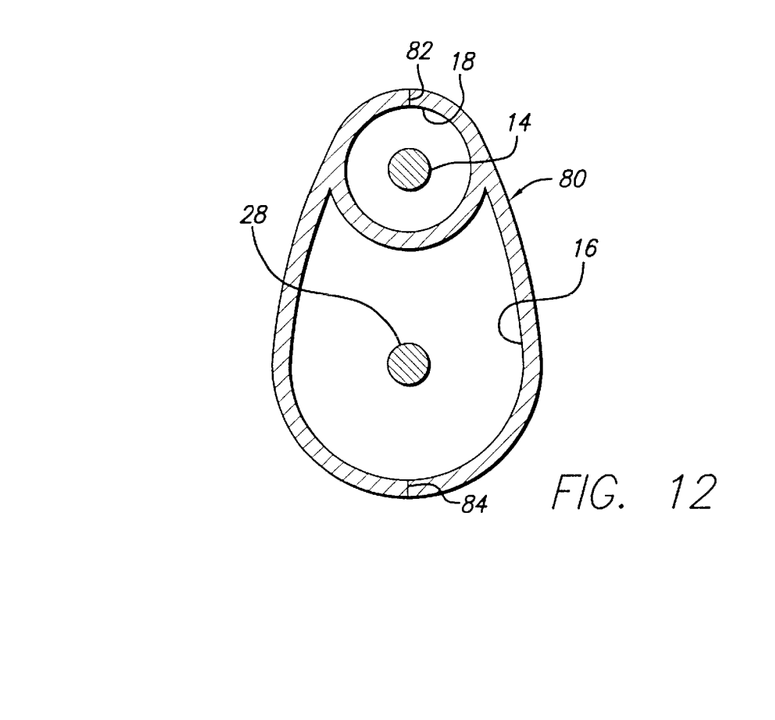
FIG. 12 is a cross-sectional view of the dual lumen delivery sheath of claim 11 taken along lines 12—12.

Referring now to FIGS. 11 and 12, an alternative embodiment of a delivery sheath 80 made in accordance with the present invention is shown. In this particular embodiment, the expandable filter device 12 is placed within a filter lumen 16 and the primary guide wire 14 is receivable within a guide wire lumen 18. The guide wire lumen 18 includes a slit 82 and the filter lumen 16 includes a slit 84 which both extend longitudinally along the tubular member forming the sheath 80. The slit 84 of the filter lumen 16 can extend along the length of the sheath 80 just proximal to the end of the filter device 12. This will create and maintain a sheath which will hold the filter device 12 in its expanded condition until it is ready to be deployed by the physician. Thereafter, once the filter device 12 has been deployed, the slit 84 will facilitate the removal of the entire delivery sheath 80 from the patient's vasculature. In like fashion, the slit 82 located along the length of the guide wire lumen 18 could also be used to facilitate the quick removal of the sheath in the event that the primary guide wire 14 is to remain within the patient's vasculature. Thereafter, an exchange of interventional devices can be quickly and easily made. It should be appreciated that either of the guide wire lumen or filter lumen could be provided with this longitudinal slit, or both, and that such a longitudinal slit could be utilized with the other embodiment disclosed herein.

Figure 13:
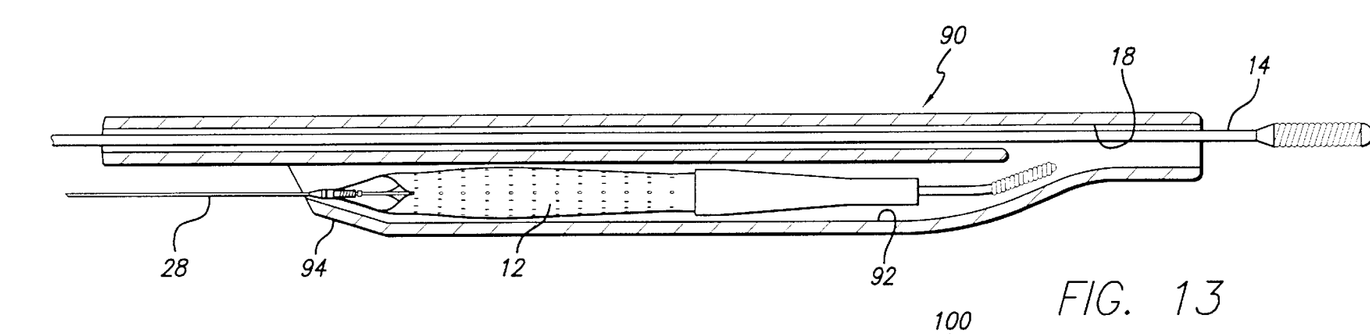
FIG. 13 is an elevational view, partially in cross-section, showing another embodiment of a dual lumen delivery sheath made in accordance with the present invention.

Referring now to FIG. 13, a rapid exchange type dual lumen delivery sheath 90 is shown which can be made in accordance with the present invention. In this particular embodiment, the filter lumen 92 is made from a short segment of tubing which creates a pod-like container for storing the collapsed filter device 12 until it is ready to be deployed. In use, the sheath portion which covers the filter 12 can be moved by retracting the proximal end of the guide wire lumen portion of the sheath as needed. This particular configuration can also utilize perforations cut or scored into the sheath, as shown in FIG. 8, in order to facilitate the easy retraction of the sheath from the filter 12. Also, as can be seen from FIG. 13, the proximal end of the filter lumen 92 has a narrower diameter than the main portion of the lumen 92 in order to help prevent the filter 12 from "backing out" of its sheath as it is being delivered within the patient's vasculature. This narrowing at the proximal region 94 does not interfere with the sheath's ability to be drawn back and retracted over the filter device 12.

Figure 14:
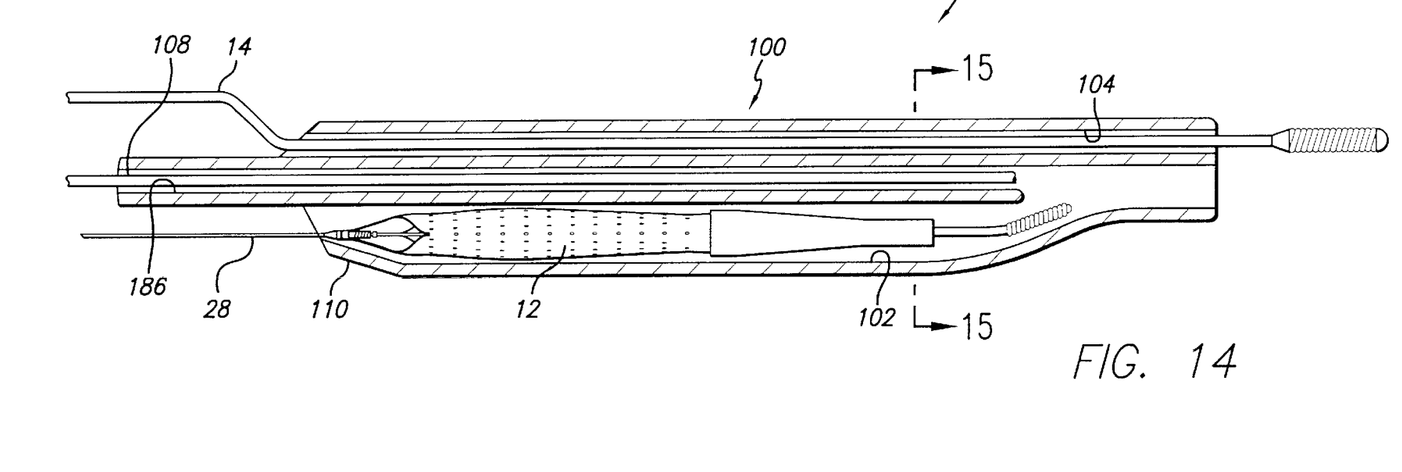
FIG. 14 is an elevation view, partially in cross-section, showing another embodiment of a delivery system made in accordance with the present invention.
Figure 15:
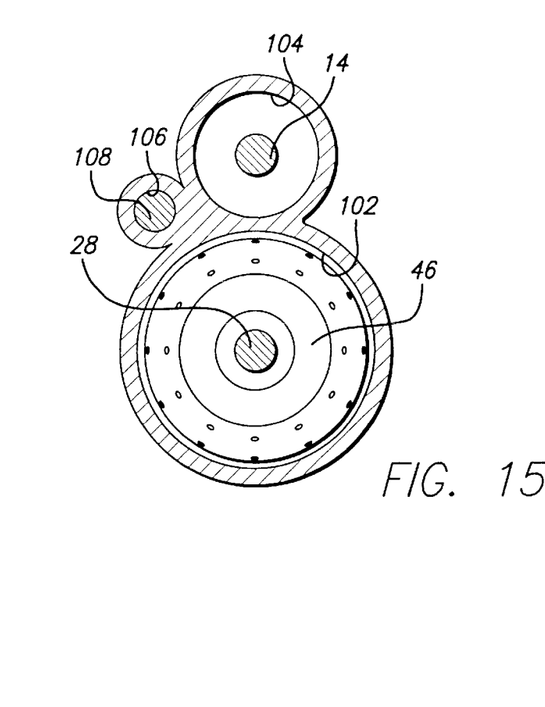
FIG. 15 is a cross-sectional view of the delivery system of FIG. 14 taken along lines 15—15.

Referring now to FIG. 14, still another embodiment of the present invention is shown in which the delivery sheath 100 includes a rapid-type exchange arrangement for both the filter lumen 102 and the primary guide wire lumen 104. This particular configuration enjoys the benefits of rapid exchange with regard to both the filter device 12 and the primary guide wire 14. This particular sheath 100 includes a third lumen 106 in which a mandrel or third guide wire 108 is utilized to provide axial stiffness to the structure as the sheath is being retracted past the collapsed filter device 12. In this manner, a three-wire delivery system can be utilized.

In use, the delivery sheath 100 and filter device 12 are delivered into the target area in the same manner as described above, namely, by moving along the primary guide wire 14 in a over-the-wire fashion. The mandrel 108 is also deployed with the delivery sheath 100 since it is adhesively fixed or bonded within the lumen 106. Once the delivery sheath 100 reaches the area in which the filter device 12 is to be deployed, the primary guide wire 14 can then be removed from the patient's vasculature. The sheath portion of the filter lumen 102 can be retracted over the filter device to deploy it within the patient's vasculature by pulling back on the proximal end of the mandrel 108. The entire delivery sheath 110 can then be removed from the patient's vasculature and the appropriate interventional devices can be advanced into the target area via the guide wire 28 of the filter device 12. The filter lumen 102 of the sheath 100 also includes a proximal area 110 in which the diameter is reduced in order to prevent the filter device 12 from backing out of the lumen 102 during usage. Again, this reduced diameter creates a composite pod-like container for the collapsed filter 12 until it is ready to be deployed within the patient's vasculature. The mandrel 108 utilized in accordance with the present invention can be any mandrel well-known in the art or an alternative could be a guide wire which is fixed within the lumen 106 of the delivery sheath 100. It should also be appreciated that the lumen 106 does not need to extend all the way back to the proximal end of the mandrel 108, but rather, it could terminate with the proximal end of the filter lumen and guide wire lumen. Thus, a composite delivery sheath can be created which provides a low profile device that can be easily advanced into the patient's vasculature.

The obturator utilized in conjunction with the present invention can be made from material such as PEBAX 40D, or other polymeric materials or alloys which are capable of providing a soft atromatic tip for the filter device. The material used to make the obturator can be loaded with radiopaque materials, such as bismuth or barium, which will help locate the tip of the device when using visualization equipment during the procedure. The obturator can be attached to the distal end of the strut assembly of the filter device utilizing adhesive or other bonding techniques to provide a strong bond between the components. The guide wire lumen formed in the obturator can be mechanically drilled or drilled utilizing a laser source.

The strut assemblies of the filter device can be made in many ways. However, the one particular method of making the strut assembly is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser.

The tubing used to make the strut assembly may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

The strut size is usually very small, so the tubing from which it is made must necessarily also have a small diameter. Typically, the tubing has an outer diameter on the order of about 0.020–0.040 inches in the unexpanded condition. The wall thickness of the tubing is about 0.076 mm (0.003–0.006 inches). For strut assemblies implanted in body lumens, such as PTA applications, the dimensions of the tubing maybe correspondingly larger. While it is preferred that the strut assembly be made from laser cut tubing, those skilled in the art will realize that the strut assembly can be laser cut from a flat sheet and then rolled up in a cylindrical configuration with the longitudinal edges welded to form a cylindrical member.

Generally, the hypotube is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The strut assembly can thus be laser cut much like a stent is laser cut. Details on how the tubing can be cut by a laser are found in U.S. Pat. No. 5,759,192 (Saunders) and U.S. Pat. No. 5,780,807 (Saunders), which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about −15° C. and 0° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding stent made in accordance with the present invention.

The strut assembly of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the strut assembly such that it is super elastic at body temperature. The transformation temperature is at or below body temperature so that the stent is superelastic at body temperature. The strut assembly is usually implanted into the target vessel which is smaller than the diameter if the strut assembly in the expanded position so that the struts apply a force to the vessel wall to maintain the filter element in the expanded position.

The strut assembly could be manufactured to remain in its open position while at body temperature and would move to its collapsed position upon application of a low temperature. One suitable method to allow the strut assembly to assume a change phase which would facilitate the strut and filter assembly being mounted into the delivery sheath include chilling the filter assembly in a cooling chamber maintained at a temperature below the martensite finish temperature through the use of liquid nitrogen. Once the strut assembly is placed in its collapsed state, the restraining sheath can be placed over the device to prevent the device from expanding once the temperature is brought up to body temperature. Thereafter, once the filter device is to be utilized, the delivery sheath is retracted to allow the filter assembly/strut assembly to move to its expanded position within the patient's vasculature.

The polymeric material which can be utilized to create the filter element include, but is not limited to, polyurethane and Gortex, a commercially available material. Other possible suitable materials include ePTFE. The material can be elastic or non-elastic. The wall thickness of the filtering element can be about 0.0005–0.005 inches. The wall thickness may vary depending on the particular material selected. The material can be made into a cone or similarly sized shape utilizing blow-mold technology. The perfusion openings can be any different shape or size. A laser, a heated rod or other process can be utilized to create to perfusion openings in the filter material. The holes, would of course be properly sized to catch the particular size of embolic debris of interest. Holes can be laser cut in a spiral pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the delivery sheath and can be made from similar polymeric material such as cross-linked HDPE. It can alternatively be made from a material such as polyolefin which has sufficient strength to hold the compressed strut assembly and has relatively low frictional characteristics to minimize any friction between the filtering assembly and the sheath. Friction can be further reduced by applying a coat of silicone lubricant, such as Microglide® or Dow 360, to the inside surface of the restraining sheath before the sheaths are placed over the filtering assembly.

In view of the foregoing, it is apparent that the system and device of the present invention substantially enhance the safety of performing certain interventional procedures by significantly reducing the risks associated with embolic material being created and released into the patient's bloodstream. Further modifications and improvements may additionally be made to the system and method disclosed herein without departing from the scope of the present invention. Accordingly, it is not intended that the invention be limited, except as by the appended claims.

What is claimed:

1. A system for delivering a filter device within a body vessel, comprising:
   a filter device mounted on an elongated member;
   a guide wire having a proximal end and a distal end; and
   a sheath having a proximal end and a distal end and including a first lumen for receiving the filter device and a second lumen for receiving the guide wire therethrough, the filter device and sheath being moveable along the guide wire for positioning the filter device within the body vessel, the sheath having a weakened region which permits at least a portion of the sheath to rupture as it is being retracted from the filter device for deploying the filter device within the body vessel.

2. The delivery system of claim 1, wherein:
   the filter device is self-expanding.

3. The delivery system of claim 1, wherein:
   the second lumen for receiving the guide wire is a short tubular segment located near the distal end of the sheath.

4. The delivery system of claim 1, wherein the weakened region is a slit formed in the sheath.

5. The delivery system of claim 1, wherein the weakened region is a line of perforations formed in the sheath.

6. The delivery system of claim 1, wherein the lumen for receiving the guide wire includes a weakened region which permits at least a portion of the sheath to rupture as the guide wire is being retracted.

7. A system for delivering a filter device within a body vessel, comprising:
   a filter device mounted on an elongated member;
   a guide wire having a proximal end and a distal end; and
   a sheath having a proximal end and a distal end and including a first lumen for receiving the filter device and a second lumen for receiving the guide wire therethrough, the filter device and sheath being moveable along the guide wire for positioning the filter device within the body vessel, the sheath being retractable from the filter device for deploying the filter device within the body vessel, wherein the second lumen for receiving the guide wire extends substantially along the length of the sheath.

8. A system for delivering a filter device within a body vessel, comprising:
   a filter device mounted on an elongated member;
   a guide wire having a proximal end and a distal end; and
   a sheath having a proximal end and a distal end and including a first lumen for receiving the filter device and a second lumen for receiving the guide wire therethrough, the filter device and sheath being moveable along the guide wire for positioning the filter device within the body vessel, the sheath being retractable from the filter device for deploying the filter device within the body vessel, wherein the first lumen for receiving the filter device extends into the second lumen for receiving the guide wire near the distal end of the sheath.

9. The delivery system of claim 8, wherein:
   the first lumen for receiving the filter device has a diameter which decreases as the first lumen extends toward the distal end of the sheath.

10. The delivery system of claim 8, wherein:
    the distal end of the first lumen is tapered at the region where it connects with the second lumen to reduce the overall diameter of the sheath at its distal end.

11. A system for delivering a filter device within a body vessel, comprising:
    a filter device mounted on an elongated member;
    a guide wire having a proximal end and a distal end; and
    a sheath having a proximal end and a distal end and including a first lumen for receiving the filter device and a second lumen for receiving the guide wire therethrough, the filter device and sheath being moveable along the guide wire for positioning the filter device within the body vessel, the sheath being retractable from the filter device for deploying the filter device within the body vessel, wherein the sheath includes perforations located near its distal end which causes at least a portion of the sheath to rupture as the tubular member is retracted from the filter device.

12. The delivery system of claim 11, wherein:

the distal end of the sheath includes a line of perforations which extend longitudinally along the length of the sheath in the distal region of the sheath.

13. A delivery sheath for delivering a filter device within a body vessel, comprising:

a tubular member having a proximal end and a distal end and including a first lumen for receiving a filter device and a second lumen for receiving a guide wire therethrough; wherein the filter device and elongated tubular member are moveable along the guide wire for positioning the filter device within the body vessel and the tubular member is retractable from the filter device to deploy the filter device within the body vessel, the tubular member including a weakened region which permits at least a portion of the tubular member to rupture as the sheath is retracted from the filter device.

14. The delivery sheath of claim 13, wherein:

the filter device is self-expanding and is mounted on a second guide wire.

15. The delivery sheath of claim 13, wherein:

the second lumen for receiving the guide wire is a short tubular segment located near the distal end of the tubular member.

16. The delivery sheath of claim 13, wherein:

the first lumen for receiving the filter device is a short tubular segment located near the distal end of the tubular member.

17. The delivery sheath of claim 13, further including a mandrel attached to the tubular member, the mandrel being adapted for delivering the tubular member over a guide wire into the body vessel.

18. A delivery sheath for delivering a filter device within a body vessel, comprising:

an elongated tubular member having a proximal end and a distal end and including a first lumen for receiving a filter device and a second lumen for receiving a guide wire therethrough; wherein the filter device and elongated tubular member are moveable along a guide wire for positioning the filter device within the body vessel and the tubular member is retractable from the filter device to deploy the filter device within the body vessel and the second lumen for receiving the guide wire extends substantially along the length of the elongated tubular member.

19. A delivery sheath for delivering a filter device within a body vessel, comprising:

an elongated tubular member having a proximal end and a distal end and including a first lumen for receiving a filter device and a second lumen for receiving a guide wire therethrough; wherein the filter device and elongated tubular member are moveable along a guide wire for positioning the filter device within the body vessel and the tubular member is retractable from the filter device to deploy the filter device within the body vessel and the first lumen for receiving the filter device extends into the second lumen for receiving the guide wire near the distal end of the tubular member.

20. The delivery sheath of claim 19, wherein:

the first lumen for receiving the filter device has a diameter which decreases as the first lumen extends towards the distal end of the tubular member.

21. The delivery sheath of claim 20, wherein:

the distal end of the first lumen is tapered at a region where it connects with the second lumen to reduce the overall diameter of the tubular member at its distal end.

22. A delivery sheath for delivering a filter device within a body vessel, comprising:

an elongated tubular member having a proximal end and a distal end and including a first lumen for receiving a filter device and a second lumen for receiving a guide wire therethrough; wherein the filter device and elongated tubular member are moveable along a guide wire for positioning the filter device within the body vessel and the tubular member is retractable from the filter device to deploy the filter device within the body vessel and the tubular member includes perforations located near its distal end which cause at least a portion of the tubular member to rupture as a tubular member is retracted from the filter device.

23. A delivery sheath for delivering a filter device within a body vessel, comprising:

an elongated tubular member having a proximal end and a distal end and including a first lumen for receiving a filter device and a second lumen for receiving a guide wire therethrough; wherein the filter device and elongated tubular member are moveable along a guide wire for positioning the filter device within the body vessel and the tubular member is retractable from the filter device to deploy the filter device within the body vessel and the first lumen for receiving the filter device is a short tubular segment located near the distal end of the tubular member, the first lumen having a first end and a second end and a primary diameter sufficient to receive the filter device in a collapsed position with a narrower diameter near the first and second ends to resist movement of the filter device from the sheath as it is being delivered within the body vessel.

24. A delivery sheath for delivering a filter device within a body vessel, comprising:

an elongated tubular member having a proximal end and a distal end and including a first lumen for receiving a filter device and a second lumen for receiving a guide wire therethrough; wherein the filter device is mounted on a second guide wire and the filter device and elongated tubular member are moveable along a guide wire for positioning the filter device within the body vessel and the tubular member is retractable from the filter device to deploy the filter device within the body, the first lumen for receiving the filter device includes a weakened region extending longitudinally from the proximal end of the tubular member to a region adjacent to the sleeve which houses the filter device for facilitating removal of the second guide wire therethrough.

25. The delivery sheath of claim 24, wherein the weakened region is a slit formed in the tubular member.

26. The delivery sheath of claim 24, wherein the weakened region is a line of perforations formed in the tubular member.

27. A delivery sheath for delivering a filter device within a body vessel, comprising:

an elongated tubular member having a proximal end and a distal end and including a first lumen for receiving a filter device and a second lumen for receiving a guide wire therethrough; wherein the filter device and elongated tubular member are moveable along a guide wire for positioning the filter device within the body vessel and the tubular member is retractable from the filter device to deploy the filter device within the body vessel and the second lumen for receiving the guide wire includes a weakened region extending longitudinally from the proximal end to the tubular member to a region adjacent to the portion of the sheath which houses the filter device to facilitate removal of the guide wire therethrough.

28. The delivery sheath of claim 27, wherein the weakened region is a slit formed in the tubular member.

29. The delivery sheath of claim 27, wherein the weakened region is a line of perforations formed in the tubular member.

30. A system for delivering a filter device within a body vessel, comprising:

a guide wire having a proximal end and a distal end;

a filter device moveable between a collapsed position and an expanded position which includes an obturator located at the distal end of the filter device, the filter device being attached to the guide wire near its distal end; and a guide wire lumen extending through the obturator which is adapted to receive a second guide wire used to deliver the filter device into the body vessel utilizing an over-the-wire technique.

31. The delivery system of claim 30, wherein the obturator has a central distal tip and the guide wire lumen extends through the central distal tip.

32. The delivery system of claim 30, wherein:

the obturator has a central distal tip and the guide wire lumen extends through the obturator offset from the central distal tip.

* * * * *